Sept. 25, 1951 E. S. BOERNER Plant Pat. 1,039
ROSE PLANT
Filed July 18, 1950
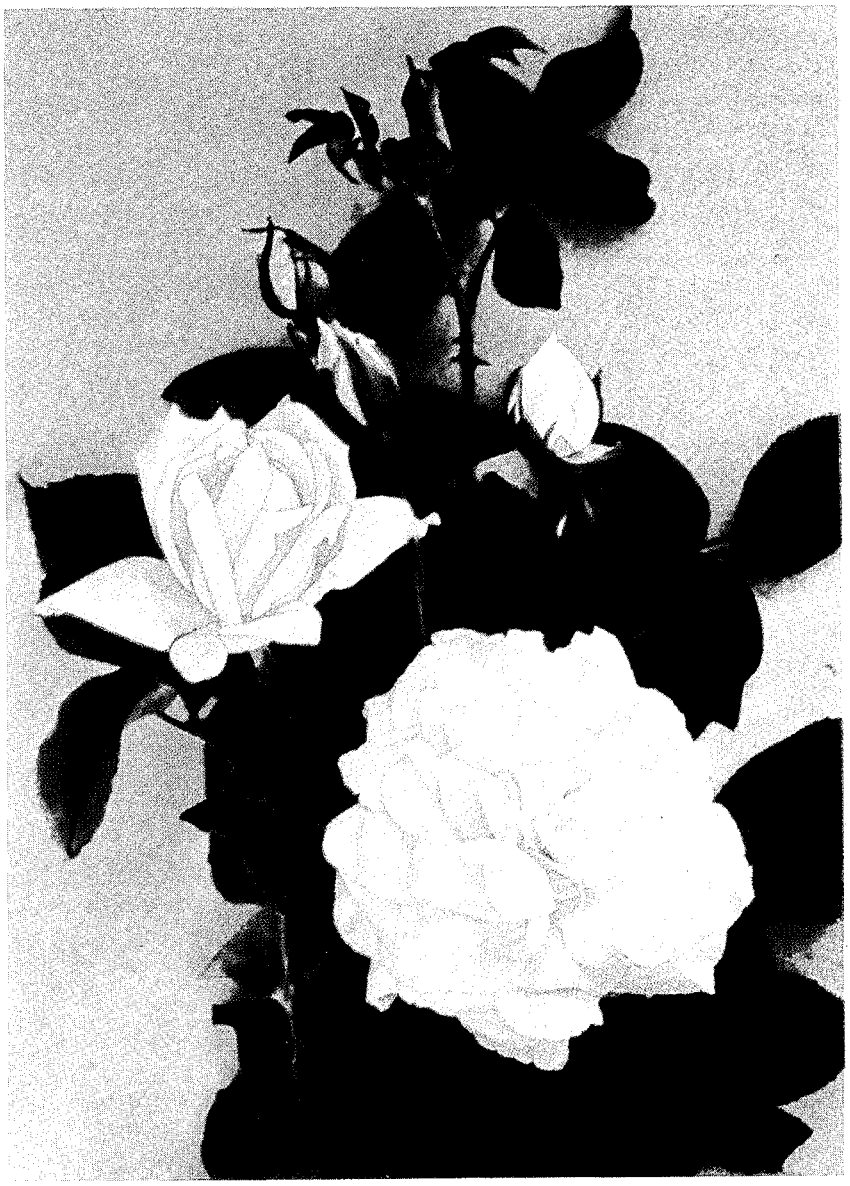
Inventor.
E. S. Boerner
By: Robb & Robb
Attorneys.

Patented Sept. 25, 1951 Plant Pat. 1,039

UNITED STATES PATENT OFFICE 1,039

ROSE PLANT

Eugene S. Boerner, Newark, N. Y., assignor to Jackson & Perkins Company, Newark, N. Y., a corporation of New York Application July 18, 1950, Serial No. 174,553

1 Claim. (Cl. 47—61)

This invention relates to a new and distinct variety of rose plant of the hybrid tea class, originated by crossing the variety "Joanna Hill" (unpatented) × ["Mrs. Pierre S. Du Pont (unpatented) × "Amelia Earhart" (Plant Patent No. No. 63)].

The objective of this cross was to obtain a forcing rose in the yellow color, and for that purpose, the variety "Joanna Hill," which is a well-known American forcing rose, was used. The resulting new variety retained the forcing quality and has much better foliage, with flowers of Empire Yellow color.

Due to its prolific production and many side branches, the new variety is especially adapted to and useful for pot forcing in greenhouses. It also has many secondary flowers and branches.

Asexual reproduction of the new variety by budding at Newark, New York, and at Pleasanton, California, shows that the foregoing characteristics come true to form and are established and transmitted through succeeding propagations.

The accompanying drawing shows specimens of this new variety, with the flowers and foliage in different stages of development.

The following is a detailed description of the new variety, with color terminology in accordance with Ridgway's Color Standards and Nomenclature:

Parentage: Seedling.

*Seed parent.*—"Joanna Hill."

*Pollen parent.*—An unnamed seedling of "Mrs. Pierre S. Du Pont × "Amelia Earhart."

Classification: Botanic and commercial—hybrid tea.

*Flower*

(Observations made from pot plants in the greenhouse at Newark, New York, in the month of March, 1950.)

Blooming habit: Recurrent—continuous.

Bud:

*Size.*—Large.

*Form.*—Ovoid. Is not affected by wet or hot weather.

*Color.*—When sepals first divide—Light Orange Yellow, Plate 3. When petals begin to unfurl—Apricot Yellow, Plate 4. When half blown—inside of petals—Apricot Yellow, Plate 4; reverse of petals—Buff Yellow, Plate 4.

*Sepals.*—Slightly branched. Curl back when petals begin to unfurl. Color—inside—Light Lumiere Green, Plate 17; outside—Light Bice Green, Plate 17.

*Calyx.*—Shape—apple. Size—large. Aspect—smooth. Odor when rubbed—none. Color—Lettuce Green, Plate 5.

*Peduncle.*—Length — medium. Aspect—smooth. Color—Lettuce Green, Plate 5. Strength—erect; slender.

*Opening.*—Bud opens up well. Is not affected by adverse weather conditions.

Bloom:

*Size.*—Large. Average size when fully expanded, 5 inches.

*Borne.*—Singly and several together.

*Stems.*—Medium length and strong.

*Form.*—When first open—high center. Permanence—retains its form to the end.

*Petalage.*—Double (full but open center). Number of petals under normal conditions, 25.

*Color.*—Center of flower—Empire Yellow, Plate 4. Outer petals—Baryta Yellow, Plate 4. Base of petals—Lemon Chrome, Plate 4. Inside of petals—Pinard Yellow, Plate 4. Reverse of petals—Maize Yellow, Plate 4. General tonality from a distance—Empire Yellow, Plate 4.

*Discoloration.*—General tonality at end of first day—Empire Yellow, Plate 4. Second day—between Empire Yellow, Plate 4, and Pinard Yellow, Plate 4. Third day—between Pinard Yellow, Plate 4, and Martius Yellow, Plate 4.

Petals:

*Texture.*—Thick. Are not affected by wet or hot weather.

*Appearance.* — Inside — satiny. Outside—shiny.

*Form.*—Round.

*Arrangement.* — Imbricated (regularly arranged shingle-like). Petaloids in center—few and large.

*Persistance.*—Drop off cleanly.

*Fragrance.*—Slight. Nature—tea (average hybrid tea scent).

*Lasting quality.*—On the plant—very long. As cut flower—long.

Genital organs:

*Stamens, anthers.*—Large size and many. Color—Empire Yellow, Plate 4. Arrangement—regular around styles.

*Stamens, filaments (threads).*—Long. Color—Spectrum Red, Plate 1.

*Pollen.*—Color—Maize Yellow, Plate 4.

*Styles.*—Loosely separated and of uneven length. Short and heavy.

*Stigmas.*—Color—Naples Yellow, Plate 4.

*Ovaries.*—Some protruding from calyx.

*Plant*

Form: Bush.
Growth: Vigorous, upright, and branching.
Foliage: 5 to 7 leaflets.
*Size.*—Large.
*Quantity.*—Normal.
*Color.*—New foliage—upper side: Lettuce Green, Plate 5; under side: Absinthe Green, Plate 31. Old foliage—upper side: Cress Green, Plate 31; under side: Chromium Green, Plate 32.
*Shape.*—Oval pointed.
*Texture.*—Upper side — leathery. Under side—smooth. Ribs and veins—prominent.
*Edge.*—Serrated (saw toothed).
*Serration.*—Single; small.
*Leaf stem.*—Color—Absinthe Green, Plate 31. Under side—prickles.
*Stipules.*—Medium length and smooth.
*Disease resistance.*—Resistant.
Wood:
*New wood.*—Color—Parrott Green, Plate 6. Bark—smooth.

*Old wood.*—Color—Dark Cress Green, Plate 31. Bark—smooth.
Thorns: Quantity on main stalks from base and on laterals from stalk—ordinary.
*Form.*—Flat base. Medium length and hooked downward.
*Color when young.*—Eugenia Red, Plate 13.
*Position.*—Irregular.
*Prickles.*—Quantity on main stalks and on laterals—none.
*Short needles.*—Quantity on main stalks and on laterals—none.

I claim:

A new and distinct variety of rose plant of the hybrid tea class, characterized as to novelty by its prolific production and many side branches which make it especially adapted to and useful for pot forcing in greenhouses, by its improved foliage, by its flowers of Empire Yellow color, and by its many secondary flowers and branches, substantially as shown and described.

EUGENE S. BOERNER.

No references cited.